United States Patent [19]

Robba et al.

[11] Patent Number: 4,474,783
[45] Date of Patent: Oct. 2, 1984

[54] CYCLOPROPYLMETHYL PIPERAZINES, THE PROCESS FOR PREPARING THE SAME AND THEIR USE IN THERAPEUTICS

[75] Inventors: Max F. Robba; Michel E. Aurousseau, both of Paris, France

[73] Assignee: Innothera, Arcueil, France

[21] Appl. No.: 305,752

[22] Filed: Sep. 25, 1981

[30] Foreign Application Priority Data

Oct. 8, 1980 [FR] France .............................. 80 21527

[51] Int. Cl.$^3$ ................. C07D 241/04; C07D 295/00; A61K 31/495
[52] U.S. Cl. ................................. 424/250; 544/121; 544/358; 544/359; 544/360; 544/372; 544/376; 544/377; 544/386; 544/391; 544/392; 544/399; 544/401; 424/248.4
[58] Field of Search ............... 544/358, 386, 389, 391, 544/399, 401; 424/250

[56] References Cited

U.S. PATENT DOCUMENTS

| | | | |
|---|---|---|---|
| 2,724,713 | 11/1955 | Goldman et al. | 544/389 |
| 4,057,413 | 11/1977 | Naumann et al. | 544/399 |
| 4,096,261 | 6/1978 | Horrom et al. | 424/250 |
| 4,163,849 | 8/1979 | Lumma, Jr. et al. | 424/250 |

OTHER PUBLICATIONS

Irwin et al., "Journal of Med. Chem.", vol. 15, No. 6, pp. 690–692, (1972), Alkyl Derivatives of Tetrahydrousoquinololine, 1-Phenylpiperazine and 4-Dyphenylmethylpiperidine.

*Primary Examiner*—Donald G. Daus
*Assistant Examiner*—S. A. Gibson
*Attorney, Agent, or Firm*—Flynn, Thiel, Boutell & Tanis

[57] ABSTRACT

A compound having the formula

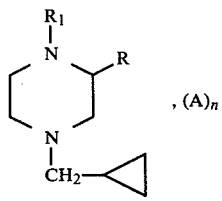

in which R is hydrogen or alkyl having 1 to 4 carbon atoms; $R_1$ is hydrogen, alkyl having 1 to 5 carbon atoms, cycloalkylmethyl in which the cycloalkyl group has from 3 to 6 carbon atoms, 2-hydroxyethyl, alkoxycarbonyl in which the alkoxy group has 1 or 2 carbon atoms, 2-carboxypropyl, N-benzyl-2-carbamoyl propyl, phenyl, phenyl substituted by methoxy, trifluoromethyl or acetyl, benzyl, benzyl substituted by halogen, benzoyl, benzoyl substituted by three methoxy groups, 3,5-dimethoxy-4-acetoxy or 3,5-dimethoxy-4-ethoxycarbonyloxy, cinnamoyl, cinnamoyl in which the phenyl ring is substituted with trifluoromethyl or by one or more methoxy groups, phenoxyacetyl, phenoxyacetyl in which the phenyl ring is substituted with halogen or methoxy, and

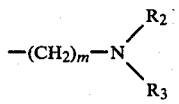

in which m is 2 or 3 and $R_2$ and $R_3$ are identical and are alkyls having 1 to 3 carbon atoms; A is a pharmaceutically acceptable compound selected from the group consisting of inorganic acids, organic acids, alkyl halides and aryl halides; and n is 0, 1, 2 or 3;

The compounds are useful in the treatment of cardiac disease symptomized by low cardiac flow.

13 Claims, No Drawings

CYCLOPROPYLMETHYL PIPERAZINES, THE PROCESS FOR PREPARING THE SAME AND THEIR USE IN THERAPEUTICS

The present invention relates to new cyclopropylmethyl piperazines, the process of preparing them and their application in therapeutics.

These new cyclopropylmethyl piperazines satisfy the general formula:

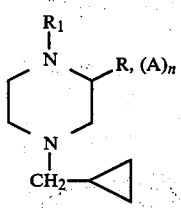

in which:

R represents an atom of hydrogen or an alkyl radical comprising from 1 to 4 carbon atoms;

$R_1$ represents:
- an atom of hydrogen
- a linear or branched alkyl radical comprising from 1 to 5 carbon atoms
- a cycloalkylmethyl radical in which the cycloalkyl group comprises from 3 to 6 carbon atoms
- a 2-hydroxy ethyl group
- an alkoxycarbonyl group in which the alkoxy group comprises 1 or 2 carbon atoms
- a 2-carboxy propyl or N-benzyl 2-carbamoyl propyl group
- a phenyl nucleus possibly substituted by a methoxy, trifluoromethyl or acetyl group
- a benzyl group possible substituted by a halogen atom and/or by a methylenedioxy group
- a benzoyl group possibly substituted by a methylenedioxy group; by three methoxy groups; by two methoxy groups respectively in positions 3 and 5 and an acetoxy group in position 4; or by two methoxy groups respectively in positions 3 and 5 and an ethoxycarbonyloxy group in position 4
- a cinnamoyl group in which the phenyl nucleus is possibly substituted by a trifluoromethyl group, or by one or more methoxy groups
- a phenoxyacetyl group in which the phenyl nucleus is possibly substituted by a halogen atom or a methoxy group
- a (3-benzothienyl) methyl nucleus or
- a radical of formula:

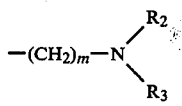

in which m=2 or 3 and $R_2$ and $R_3$ are identical and then represent an alkyl group having from 1 to 3 carbon atoms, or form together with the nitrogen atom to which they are linked, a radical selected from the following: pyrrolidino, piperidino, hexamethyleneimino, morpholino;

A represents a physiologically acceptable compound selected among the inorganic acids, the organic acids, the alkyl halides and the aryl halides; and n=0, 1, 2 or 3; with the proviso that $R_1$ cannot represent a phenyl nucleus or a hydrogen atom when R=H.

The following preferred compound A may be mentioned as inorganic acids—hydrochloric acid, hydrobromic acid, sulfuric acid and phosphoric acid; as organic acids—lactic acid, tartaric acid, pyruvic acid, glycolic acid, oxalic acid, citric acid, malonic acid, malic acid, succinic acid, maleic acid, fumaric acid, embonic acid and methane sulfonic acid; as regards the alkyl halides, methyl bromide, ethyl bromide and butyl bromide; finally as regards the aryl halides—benzyl bromide.

In cases where n in formula (I) takes the value zero, the corresponding compounds are in their base form and in cases where n takes the value 1, 2 or 3, the corresponding compounds are in the form of ammonium salts.

The compounds of formula (I) in which $R_1$ represents a hydrogen atom are obtained by condensation of at the most 1 mole of bromomethylcyclopropane on 1 mole of piperazine of formula:

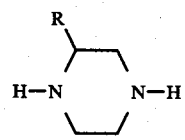

where R designates an alkyl radical comprising from 1 to 4 atoms, the resulting compounds having the formula:

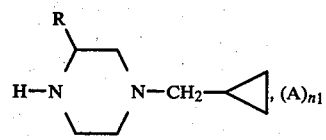

where R has the same meaning as in formula (II) and $n_1=0$, being subsequently possibly salified by addition of a compound of formula A defined in formula (I), which leads to compounds of formula:

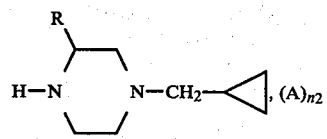

where R and A have the same meaning as in formula (II) and formula (I) respectively and $n_2$ is equal to 1 or 2 according to the amount of compound A added.

The above condensation reaction is carried out in an organic solvent, inert in the conditions of the reaction and capable of rendering soluble the reagents, such as for example ethyl acetate. Moreover, the process will be carried out preferably at a temperature not too high (for example ambient temperature) in order to prevent a second molecule of bromomethylcyclopropane from condensing on the compound of formula (II), and in the presence of a base which may be either inorganic and of the dipotassium carbonate type, or organic and of the trietylamine type. Finally, as regards yield, it is recommended to use an excess of piperazine of formula (II) compared with the bromomethylcyclopropane, with these compounds for example in a molar ratio of about 1 to 0.35.

The compounds of formula (I) in which $R_1$ represents a cyclopropylmethyl group, are for their part, obtained by condensing at least 2 moles of bromomethylcyclopropane respectively on 1 mole of piperazine and 1 mole of the compound of formula (II), the resulting compounds having the formula:

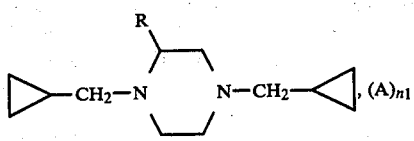
(Ic)

where R has the same meaning as in formula (I) and $n_1=0$, being subsequently possibly salified by addition of a compound of the formula A already defined in formula (I), which leads to compounds with the formula:

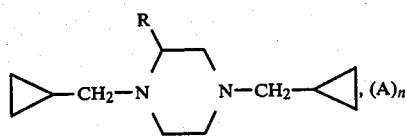
(Id)

where R and A have the same meaning as in the formula (I) and $n_2$ is equal to 1 or 2 according to the amount of compound A added.

The condensation reaction may be carried out using the same procedure as previously (as regards solvent and base). It is nonetheless preferable to proceed at a higher temperature in order to promote the double condensation of the bromomethylcyclopropane; the solvent used may then be chosen from those having a fairly high boiling point, for example N,N-dimethylformamide.

The compounds according to the invention for which $R_1$ has the same meaning as in formula (I), with the exception of the following values: H, phenyl and phenyl substituted by a methoxy, trifluoromethyl or acetyl group, are for their part obtained by condensing N-cyclopropylmethyl piperazine or a piperazine of formula (Ia) with a compound of formula:

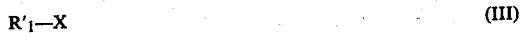
(III)

where X represents a halogen atom and $R'_1$ has the same meaning as $R_1$ in formula (I), except for the following values: H, phenyl and phenyl substituted by a methoxy, trifluoromethyl or acetyl group, which leads to compounds of formula:

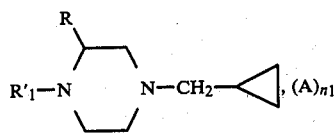
(Ie)

where $R'_1$ and R have the same meaning as in formulae (III) and (I) respectively and $n_1=0$, these compounds of formula (Ie) being subsequently possibly salified by addition of a compound of formula A defined previously in order to lead to compounds of formula:

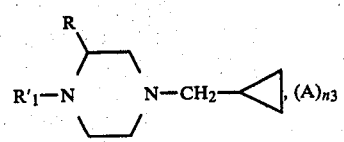
(If)

where $R'_1$ and R have the same meaning as in formula (Ie), A has the same meaning as in formula (I) and $n_3$ is equal to 1, 2 or 3 according to the amount of compound A added and/or the reactivity of the base of formula (Ie).

Condensation of the compounds of formulae (Ia) and (III) is carried out in an organic solvent inert in the reaction conditions and appropriate for dissolving the reagents. More precisely, when in formula (III) $R'_1$ contains a carbonyl group linked directly to X, corresponding compounds $R'_1$—X are generally highly reactive and in this case it will be preferable to carry out the condensation in a solvent such as ethyl acetate and at a low temperature, for example between 0° C. and ambient temperature. When this group $R'_1$ contains a $CH_2$ group linked directly to X, the resulting compounds of formula (III) are less reactive and the condensation is then carried out in a solvent such as isopropanol and under reflux.

Finally, the compounds according to the invention for which $R_1$ has the same meaning as in formula (I), with the exception of the values H and

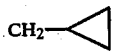

can also be obtained by condensing the bromomethylcyclopropane on a substituted piperazine of formula:

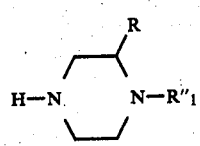
(IV)

in which R has the same meaning as in formula (I) and $R''_1$ has the same meaning as $R_1$ in formula (I), with the exception of the values—H and

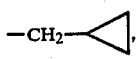

the resulting compounds having the formula:

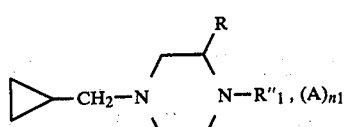
(Ig)

where R and $R''_1$ have the same meaning as in formula (IV) and $n_1=0$, possibly being salified by addition of a compound of formula (A) already defined above, which leads to compounds of the following formula:

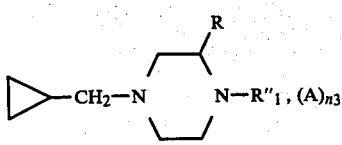

in which R and A have the same meaning as in formula (I), R"₁ has the same meaning as in formula (IV) and n₃ is equal to 1, 2 or 3 according to the amount of compound A added.

The condensation reaction is carried out in an organic solvent, inert in the conditions of the reaction and capable of dissolving the reagents, such as N,N-dimethylformamide.

The procedure will be carried out preferably under reflux and in the presence of an inorganic or organic base, of the dipotassium carbonate or triethylamine type.

The optional salification of the bases of formulae (Ia), (Ic), (Ie) and (Ig) is carried out using conventional techniques, for example by the action of the compounds of formula (A) in solution in appropriate solvent, on the base possibly in solution in a suitable organic solvent.

The following preparations are given as examples to illustrate the invention.

EXAMPLE 1

1,4-Dicyclopropylmethyl piperazine (Ic)

Code number: 3

A mixture of 51.6 g of anhydrous piperazine, 216 g of bromomethylcyclopropane and 128 g of dipotassium carbonate in 400 ml of dimethylformamide is heated for 30 hours at 110° C. with stirring. After cooling, the mixture is filtered, the solvent and unused reagents eliminated under vacuum and then rectified. The desired compound is collected in the form of a colourless oil.

Yield: 60%
Bp (18 mm Hg)=137°-140° C.

Using the same process but with similar reagents, the base corresponding to the compound with code No. 13 in table I below is obtained.

The bis-hydrochloride (ID) [code No.: 3a] of the base (Ic) prepared is obtained by adding a solution of 120 ml of absolute alcohol saturated with gaseous hydrochloric acid to a solution of 30 g of the base obtained above in 700 ml of ethyl alcohol. The desired bis-hydrochloride is obtained and can be recrystallized in ethanol. This salt is in the form of white crystals with a melting point of 286° C.

Using the same process but with the corresponding base, the compound of code number 13 shown in table I below is obtained.

The bis-oxalate (Id) [code No. 3b] of the base (Ic) prepared above is obtained by heating under reflux for 15 minutes, a solution of 5 g of 1,4-dicyclopropylmethyl piperazine and 5 g of oxalic acid in 150 ml of acetone. In this way, the required salt is isolated and can be recrystallized in water. It is in the form of white crystals and melts at 266° C.

The bis-citrate (Id) [code No. 3c] of the 1,4-dicyclopropylmethyl piperazine base is obtained by heating under reflux for 15 minutes, a solution of 5 g of this base and 5 g of citric acid in acetone. The required salt is produced and can be recrystallized in water. It is in the form of white crystals which melt at 163° C.

The bis-bromomethylate (Ic) [code No. 3d] of the 1,4-dicyclopropylmethyl piperazine base is obtained by passing a stream of methyl bromide for 15 minutes into a solution of 5 g of the said base in 100 ml of acetone. The product obtained is concentrated, filtered and recrystallized in acetonitrile. In this way, the desired salt is isolated and is in the form of white crystals which melt at 225° C.

EXAMPLE 2

1-Cyclopropylmethyl methyl-3 piperazine (Ia)

Code number: 23

A mixture of 46 g of bromomethylcyclopropane, 100 g of anhydrous 3-methyl piperazine and 23.4 g of dipotassium carbonate in 400 ml of ethyl acetate is stirred for 5 hours at ambient temperature. The mixture is filtered, the organic phase washed with a 4N aqueous solution of NaOH, the solvent eliminated and the mixture vacuum distilled.

In this way the required product is obtained.

EXAMPLE 3

1-Cyclopropylmethyl 4-carbethoxy piperazine

Code number: 6

A mixture of 25.5 g of bromomethylcyclopropane, 30.5 g of N-carbethoxypiperazine (IV) and 2.5 g of dipotassium carbonate in 25 ml of N,N-dimethylformamide is heated under reflux for 6 hours with stirring. The mixture is filtered, the solvent eliminated and vacuum distilled. In this way the required product is isolated and is in the form of a colourless oil with a boiling point at 11 mmHg of 142° to 148° C.

Using the same process, but with similar reagents, the bases corresponding to the compounds of code Nos. 2, 4, 5, 7 to 8, 10 to 12, 14, 35 to 37, 40 and 41 in table I are obtained.

EXAMPLE 4

Hydrochloride of 1-cyclopropylmethyl 4-p-fluorophenoxyacetyl piperazine

Code number: 22

A solution of 9.64 g of chloride of para-fluorophenoxyacetyl (III) in 25 ml of ethyl acetate is poured at 0° C. into a solution of 7.5 g of cyclopropylmethylpiperazine in 25 ml of ethyl acetate with continuous stirring. When all the reagents are present, the mixture is stirred for one hour at 20° C. The mixture is filtered, washed with ether and the requied derivative is dried and obtained in the form of hydrochloride. It is recrystallized in a mixture of absolute alcohol and ethylic ether (1/1), which produces white crystals melting at 139° C.

Using the same process, but with similar reagents, the compounds with code Nos. 15 to 21, 38 and 39 in table I below are obtained.

EXAMPLE 5

Trihydrochloride of 1-cyclopropymethyl 3-methyl 4-(2-N-piperidino ethyl) piperazine Code number: 27

A solution of 4.62 g of 1-cyclopropylmethyl 3-methyl piperazine and 4.90 g of 2-N-piperidino chloroethane in 100 ml of isopropanol is heated under reflux for 17 hours. The mixture is then evaporated to dryness under vacuum, the residue added to 2N NaOH and extracted with ethyl ether. The solvent is eliminated and the resultant product converted into a hydrochloride with a solution of alcohol saturated with anhydrous gaseous hydrochloric acid. The trihydrochloride obtained and recrystallized in 95° alcohol melts at 264° C.

Using the same process, but with similar reagents, the compounds with code Nos. 24 to 26 and 28 to 34 in table I below are obtained.

TABLE I $$\text{(I)}$$

structure: piperazine ring with N-CH$_2$-cyclopropyl at top N, and bottom N bearing R$_1$; ring carbon bears (A)$_n$ and R

| Code No. | R | R$_1$ | (A)$_n$ | Crystallization solvent | Melting point (°C.) | Yield (%) |
|---|---|---|---|---|---|---|
| 2 | H | CH$_3$ | 2HCl | Acetonitrile/95° ethyl alcohol (1/9) | 238 | 30 |
| 3 | " | —CH$_2$—◁ | Base | — | 137–140* | 60 |
| 3a | " | —CH$_2$—◁ | 2HCl | Ethyl alcohol | 286 | 65 |
| 3b | " | " | 2(COOH)$_2$ | Water | 266 | 40 |
| 3c | " | " | Bis-citrate | " | 163 | 30 |
| 3d | " | " | Bis-bromomethylate | Acetonitrile | 225 | 75 |
| 3e | " | " | bis-sulfomethylate | Absolute alcohol | 252 | 30 |
| 3f | " | " | bis-lactate | Acetonitrile | 78 | 30 |
| 3g | " | " | bis-tartrate | Absolute alcohol | 93 | 50 |
| 3h | " | " | bis-pyruvate | 95° alcohol | 191 | 25 |
| 3i | " | " | bis-maleate | 95° alcohol | 224 | 50 |
| 3j | " | " | bis-glycolate | Absolute alcohol | 120 | 80 |
| 4 | " | —(CH$_2$)$_4$CH$_3$ | 2HCl | Absolute alcohol | >300 | 50 |
| 5 | " | —CH$_2$CH$_2$OH | 2HCl | Absolute alcohol/acetonitrile (1/1) | 191 | 20 |
| 6 | " | —COOC$_2$H$_5$ | Base | — | 142–148* | — |
| 6a | " | —COOC$_2$H$_5$ | HCl | Acetonitrile | 192 | 70 |
| 7 | H | —CH$_2$CH(CO$_2$H)(CH$_3$) | 2HCl | Absolute alcohol | 232 | 35 |
| 8 | " | —CH$_2$CH(CH$_3$)CONHCH$_2$C$_6$H$_5$ | 2(COOH)$_2$ | 95° alcohol | 169.9 | 30 |
| 10 | " | 2-methoxyphenyl (OCH$_3$) | 2HCl | Acetonitrile | 202 | 50 |

TABLE I-continued (Structure I: piperazine with N-CH₂-cyclopropyl at top N, (A)ₙ and R substituents on ring, R₁ on bottom N)

| Code No. | R | R₁ | (A)ₙ | Crystallization solvent | Melting point (°C.) | Yield (%) |
|---|---|---|---|---|---|---|
| 11 | " | 3-(CF₃)-phenyl | HCl | Acetonitrile | 176 | 48 |
| 12 | " | 4-(COCH₃)-phenyl | HCl | Absolute alcohol | 183 | 20 |
| 12a | " | 4-(COCH₃)-phenyl | HBr | Absolute alcohol | 232 | 30 |
| 13 | CH₃ | —CH₂-cyclopropyl | 2HCl | 95° alcohol | 246.6 | 70 |
| 14 | H | —CH₂-phenyl | 2HCl | 95° alcohol | 250 | 40 |
| 15 | " | —CO-(3,4-methylenedioxyphenyl) | HCl | Acetonitrile | 231 | 45 |
| 16 | " | —CO-(3,4,5-trimethoxyphenyl) | (COOH)₂ | Dioxanne/water (3/1) | 260 | 45 |
| 17 | " | —CO-(3,4,5-trimethoxyphenyl) | HCl | Absolute alcohol | 201 | 35 |
| 18 | " | —CO-(2,6-dimethoxy-4-OCO₂C₂H₅-phenyl) | HCl | Absolute alcohol | 230 | 35 |
| 19 | " | —COCH=CH-(3-CF₃-phenyl) | HCl | Acetonitrile | 215 | 40 |

TABLE I-continued (Structure I: 1-(cyclopropylmethyl)piperazine with (A)n, R substituent at position adjacent to N-R1)

| Code No. | R | R₁ | (A)ₙ | Crystallization solvent | Melting point (°C.) | Yield (%) |
|---|---|---|---|---|---|---|
| 20 | " | —COCH=CH—(3,4,5-trimethoxyphenyl) | HCl | 95° alcohol | 221 | 45 |
| 21 | " | —COCH₂O—(4-methoxyphenyl) | HCl | Absolute alcohol/ethylic ether (1/1) | 68 | 50 |
| 22 | " | —COCH₂O—(4-fluorophenyl) | HCl | Absolute alcohol/ethylic ether (1/1) | 139 | 30 |
| 23 | CH₃ | H | 2HCl | 95° alcohol | 238 | 60 |
| 24 | " | —CH₂CH₂N(CH₃)₂ | 2(COOH)₂ | 95° alcohol | 180 | 35 |
| 25 | " | —CH₂CH₂N(C₂H₅)₂ | (COOH)₂ | 95° alcohol | 201 | 60 |
| 26 | " | —CH₂CH₂N(pyrrolidinyl) | 2(COOH)₂ | 95° alcohol | 195 | 45 |
| 27 | " | —CH₂CH₂N(piperidinyl) | 3HCl | 95° alcohol | 264 | 60 |
| 28 | " | —CH₂CH₂N(hexamethyleneimino) | 2(COOH)₂ | Alcohol | 195 | 55 |
| 29 | " | —CH₂CH₂N(morpholino) | 2(COOH)₂ | 80° alcohol | 211 | 65 |
| 30 | " | —CH₂CH₂CH₂N(C₂H₅)₂ | 3(COOH)₂ | 95° alcohol | 148 | 45 |
| 31 | " | —CH₂CH₂CH₂N(pyrrolidinyl) | 3(COOH)₂ | 95° alcohol | 262 | 60 |
| 32 | " | —CH₂CH₂CH₂N(piperidinyl) | 3(COOH)₂ | 95° alcohol | 144 | 60 |

TABLE I-continued

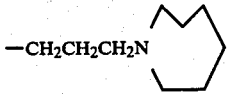

| Code No. | R | $R_1$ | $(A)_n$ | Crystallization solvent | Melting point (°C.) | Yield (%) |
|---|---|---|---|---|---|---|
| 33 | " | —CH$_2$CH$_2$CH$_2$N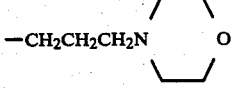 | 3(COOH)$_2$ | 95° alcohol | 149 | 65 |
| 34 | " | —CH$_2$CH$_2$CH$_2$N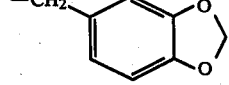O | 3(COOH)$_2$ | 95° alcohol | 191 | 60 |
| 35 | " | —CH$_2$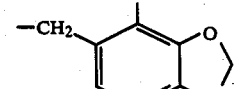 | 2(COOH)$_2$ | 95° alcohol | 160 | 60 |
| 36 | " | —CH$_2$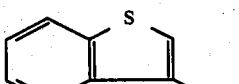 | 2(COOH)$_2$ | 95° alcohol | 114 | 60 |
| 37 | " | 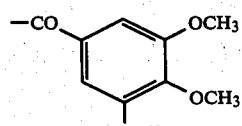 | 2(COOH)$_2$ | 95° alcohol | 169 | 58 |
| 38 | " | —CO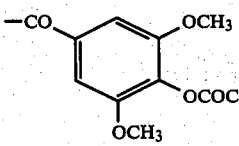OCH$_3$ / OCH$_3$ / OCH$_3$ | 2(COOH)$_2$ | 95° alcohol | 195 | 55 |
| 39 | " | —CO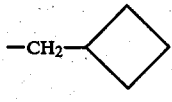OCH$_3$ / OCOCH$_3$ / OCH$_3$ | (COOH)$_2$ | 95° alcohol | 158 | 45 |
| 40 | H | —CH$_2$—□ | HCl | 95° alcohol | >300 | 40 |
| 41 | H | —CH$_2$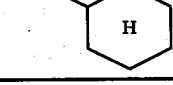H | HCl | Absolute alcohol | >300 | 50 |

*Boiling point at 18 mmHg
**Boiling point at 11 mmHg

Study of the compounds according to the invention has demonstrated a cardiotropic activity, namely positive inotrope.

The inotropic activity was demonstrated by studying the action of the said compounds on the contractile force of the isolated left auricle of the Guinea pig. The technique used is that of P. Lumley, K. J. Broadley and G. P. Lévy described in Cardiovascular Research, 11, 17–25, 1977. This technique is used to study the $\beta_1$ cardiac inotrope function; the $\beta_1$ receptors being cardiac in the Guinea pig as in man, the results obtained with the Guinea pig are applicable to man.

Guinea pigs of either sex are killed by a knock and bled; the left auricle is rapidly removed and immediately immersed in a Kreibs-Henseleit solution, the temperature being thermostatically maintained at 36° C. and aerated by a mixture of $O_2$ and $CO_2$ (95% and 5%). Two linen threads are attached to its ends: one is used to make contact between the auricle and a silver negative stimulating electrode, the other serves to connect the preparation to an isometric myograph (F-50 NARCO) and then to a recording system (Physiograph type M-K III NARCO).

Some 60 minutes are needed to ensure stability of the preparation.

Throughout the test, the auricle is activated electrically by a neurostimulator (Equipment Industriel II): voltage: supramaximum—width: 5 milli/sec.—frequency: 90 to 120 beats per minute.

Agonists, reference substances or compounds according to the invention, are added to the nutrient medium using the cumulative method of Van Rossum (Arch. Inter. Pharmacodyn., 143, 299–330, 1963). After adding each given amount of agonists, three minutes are allowed to pass before a further given amount of the product under study is added according to the method described above. The response of the organ to each concentration was assessed by the resultant increase in contractile force measured in gram. This was expressed as a percentage of the maximum increase (100%) for each compound and a dose-action curve was plotted. The agonist effect was quantified by calculating $pD_2$ (E. J. Ariens and J. M. Van Rossum., Arch. Intern. Pharmacodyn. CX, No. 2, 2, 19 and Arch. Inter. Pharmacodyn. 143, 299–330, 1963) which characterizes the affinity of the compound under test for the receptors.

The agonist effect was also characterized by the intrinsic activity (60) which defines the relative power of the agonist with respect to a standard which, in the tests, was dopamine, the intrinsic activity of which is taken arbitrarily to be $\alpha=1$.

For each compound studied, a minimum of three dose-action curves were determined, and hence three values of $pD_2$, alternating with the standard (dopamine). The results obtained are shown in table II below, it being assumed that:

the higher the value of $pD_2$ and the more marked the affinity of the compound under test for the receivers, and the higher the value of $\alpha$, the better is the intrinsic activity.

A toxicological study was also carried out on the compounds according to the invention.

More particularly, the acute toxicity was studied by introduction into the veins of male mice (10 animals per group), E.O.P.S. of the Swiss strain (bred by EVIC-CEBA).

The compounds to be tested were rendered soluble in physiological serum at variable concentrations and the solution obtained injected into the veins in an amount of 10 ml per kg of body weight. Administration was carried out in 20 seconds.

The animals were kept under clinical observation for three hours after administration and then daily for 7 days.

The lethal doses 50 ($LD_{50}$) were calculated using the method of Litchfield and Wilcoxon (J. Pharmacol. Exp. Therap., 96–99, 1949) on the basis of the different mortality rates observed.

The results of this study are also given in table II below.

TABLE II

| Code No. of compound tested | Inotropic action | | *Toxicity - $LD_{50}$ (mg/kg/i.v.) |
|---|---|---|---|
| | $pD_2$ | $\alpha$ | |
| 2 | 3.95 | 0.48 | 320 (313–327) |
| 3a | 4.52 | 0.69 | 110 (105–116) |
| 4 | — | — | 37.5 (33.0–42.0) |
| 5 | — | — | 460 (439–482) |
| 6a | 2.90 | 0.58 | 41.0 (35.9–46.8) |
| 7 | — | — | 190 (185–195) |
| 8 | 4.27 | 0.57 | 245 (240–250) |
| 10 | — | — | 34.0 (32.0–37.0) |
| 11 | — | — | 30.0 (24.2–36.3) |
| 12 | 4.26 | 0.82 | 90.0 (86.0–95.0) |
| 13 | 5.44 | 0.36 | 104 (99.7–108.4) |
| 14 | — | — | 46.0 (41.4–51.2) |
| 15 | 3.44 | 0.88 | 155 (149–161) |
| 16 | 5.06 | 0.52 | 100 mg/kg = 30% mortality |
| 17 | 3.50 | 0.19 | 245 (236–255) |
| 18 | — | — | 225 (219–232) |
| 19 | — | — | 95.0 (90.0–100.0) |
| 20 | 3.11 | 0.49 | 52.0 (47.2–57.2) |
| 21 | 4.65 | 0.69 | 115 (108–122) |
| 22 | 4.75 | 0.48 | 100 (95–106) |
| 23 | 3.75 | 0.75 | 280 (274–286) |
| 24 | — | — | 200 (193–208) |
| 25 | — | — | 150 (143–158) |
| 26 | 4.85 | 0.32 | 158 (153–163) |
| 27 | 4.32 | 0.40 | 155 (149–161) |
| 28 | — | — | 95 (89–101) |
| 29 | — | — | 250 (236–265) |
| 30 | — | — | 135 (129–141) |
| 31 | 4.57 | 0.25 | 165 (160–170) |
| 32 | 6.28 | 0.12 | 162 (152–173) |
| 33 | — | — | 130 (123–137) |
| 34 | 5.29 | 0.24 | 215 (209–221) |
| 35 | 5.28 | 0.17 | 77.0 (71.3–83.1) |
| 36 | — | — | 65.0 (61.0–70.0) |
| 37 | — | — | 40.0 (34.0–47.0) |
| 38 | — | — | 130 (122–139) |
| 39 | 4.59 | 0.69 | 225 (219–231) |

*95% confidence limit

The research described above demonstrates the value of the compounds of formula (I) according to the invention in human and animal therapeutics, notably for the treatment of cardiac diseases and in particular cardiac weaknesses and troubles characterized by a low cardiac flow.

The compounds according to the invention may be prepared for oral or parenteral administration in man and animals, possibly in association with the appropriate excipients.

For example, they may be prepared in the form of tablets, capsules, gelules or solutions for injection.

The present invention therefore comprises the therapeutic application of the compounds of formula (I), as well as the pharmaceutical compositions containing one or more of these compounds in combination with an appropriate carrier.

The daily dose may be between 100 mg and 1 g according to circumstances.

The following is an example of a pharmaceutical preparation for oral administration:

| | |
|---|---|
| 1,4-Dicyclopropylmethyl piperazine, bis-hydrochloride | 250 mg |
| Lactose | 50 mg |
| Starch | 45 mg |

| | |
|---|---|
| -continued | |
| Magnesium stearate for a 350 mg tablet. | 5 mg |

We claim:

1. A compound having the formula

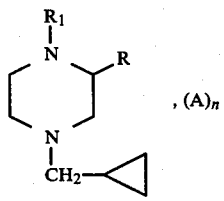

in which

R is hydrogen or alkyl having 1 to 4 carbon atoms;

$R_1$ is hydrogen, alkyl having 1 to 5 carbon atoms, cycloalkylmethyl in which the cycloalkyl group has from 3 to 6 carbon atoms, 2-hydroxyethyl, alkoxycarbonyl in which the alkoxy group has 1 or 2 carbon atoms, 2-carboxypropyl, N-benzyl-2-carbamoyl propyl, phenyl, phenyl substituted by methoxy, trifluoromethyl or acetyl, benzyl, benzyl substituted by halogen, benzoyl, benzoyl substituted by three methoxy groups, 3,5-dimethoxy-4-acetoxy or 3,5-dimethoxy-4-ethoxycarbonyloxy, cinnamoyl, cinnamoyl in which the phenyl ring is substituted with trifluoromethyl or by one or more methoxy groups, phenoxyacetyl, phenyoxyacetyl in which the phenyl ring is substituted with halogen or methoxy, and

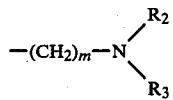

in which m is 2 or 3 and $R_2$ and $R_3$ are identical and are alkyls having 1 to 3 carbon atoms;

A is a pharmaceutically acceptable compound selected from the group consisting of inorganic acids, organic acids, alkyl halides and aryl halides; and n is 0, 1, 2 or 3; with the proviso that when R is hydrogen, $R_1$ is not hydrogen or phenyl.

2. A compound according to claim 1, in which A is selected from the group consisting of hydrochloric acid, hydrobromic acid, sulfuric acid, phosphoric acid, lactic acid, tartaric acid, pyruvic acid, glycolic acid, oxalic acid, citric acid, malonic acid, malic acid, succinic acid, maleic acid, fumaric acid, embonic acid, methane sulphonic acid, methyl bromide, ethyl bromide, butyl bromide and benzyl bromide.

3. A compound according to claim 1, which is 1,4-dicyclopropylmethyl piperazine bis-hydrochloride.

4. A compound according to claim 1 in which R is hydrogen and $R_1$ is $CH_3$.

5. A compound according to claim 1 in which R is hydrogen and $R_1$ is $COOC_2H_5$.

6. A compound according to claim 1 in which R is hydrogen and $R_1$ is p-acetylphenyl.

7. A compound according to claim 1 in which R is $CH_3$ and $R_1$ is cyclopropylmethyl.

8. A compound according to claim 1 in which R is $CH_3$ and $R_1$ is hydrogen.

9. A compound according to claim 1 in which $R_1$ is cycloalkylmethyl in which the cycloalkyl group has from 3 to 6 carbon atoms.

10. A compound according to claim 1 in which $R_1$ is alkoxycarbonyl in which the alkoxy group has 1 or 2 atoms.

11. A compound according to claim 1 in which $R_1$ is phenyl substituted by methoxy, trifluoromethyl or acetyl.

12. A pharmaceutical composition for treating cardiac disease symptomized by low cardiac flow which comprises a therapeutically effective amount of a compound as claimed in claim 1, for improving the cardiac output, in combination with a pharmaceutically acceptable vehicle.

13. A method of treating a patient afflicted with cardiac disease symptomized by low cardiac flow which comprises administering to said patient a pharmaceutical composition as claimed in claim 9.

* * * * *

UNITED STATES PATENT AND TRADEMARK OFFICE
CERTIFICATE OF CORRECTION

PATENT NO. : 4 474 783

DATED : October 2, 1984

INVENTOR(S) : Max F. Robba et al

It is certified that error appears in the above-identified patent and that said Letters Patent is hereby corrected as shown below:

Column 18, line 29; change "atoms" to ---carbon atoms---.

Signed and Sealed this

Eleventh Day of June 1985

[SEAL]

Attest:

DONALD J. QUIGG

Attesting Officer   Acting Commissioner of Patents and Trademarks